United States Patent [19]

Halligan

[11] Patent Number: Plant 6,629

[45] Date of Patent: Feb. 28, 1989

[54] RHODODENDRON PLANT 'SCENTED SPRINGTIME'

[76] Inventor: James P. Halligan, P.O. Box 489, Freeland, Wash. 98249

[21] Appl. No.: 108,982

[22] Filed: Oct. 16, 1987

[51] Int. Cl.[4] ..... A01H 5/00

[52] U.S. Cl. ..... Plt./55

[58] Field of Search ..... Plt. 55

*Primary Examiner*—Robert E. Bagwill

[57] ABSTRACT

The new cultivar 'Scented Springtime' was derived from a cross of *Rhododendron keiskei* 'Yaku Fairy' with R. 'Else Frye.' It is distinguished by its prostrate habit, fragrant flowers, and ease of propagation.

1 Drawing Sheet

BACKGROUND OF THE INVENTION

This invention is a new and distinct variety of rhododendron plant originated by me in 1983 as a consequence of a breeding program begun in 1980. The parentage of my new Rhododendron is as follows: The seed parent was *R. keiskei* 'Yaku Fairy' and the pollen parent was R. 'Else Frye.' This was intended as a preliminary cross to combine the compactness and hardiness of R. 'Yaku Fairy' with the large fragrant flowers of R. 'Else Frye.' Fragrance was not expected at this stage in the breeding program, and was not present in any of its siblings. This plant is quite different from its siblings, having larger broader leaves, larger more highly colored flowers, faster growth rate, more flowers to the truss, and fragrance. Observers have found the fragrance reminiscent of gardenias.

My new variety is characterized by a prostrate growth habit and fragrant flowers. The flower color of pale yellow with fuchsia streaks is pleasant but unremarkable. It is unlike any other Rhododendron known to me. It shows the prostrate growth habit of its seed parent and the fragrance of its pollen parent. Flower and leaf size are intermediate between its parents, as is flower color.

Asexual propagation by cuttings at Langley, Wash. and Snohomish, Wash. shows that all characteristics of the variety come true through succeeding generations. This plant is currently being grown by me at 5837 West Useless Bay Ave., Langley, Wash. 98260. It has also been loaned to two other persons for evaluation and breeding purposes. Their names and addresses are as follows: Dr. R. L. Ticknor, 844 N. Holly St., Canby, Oreg. 97013 and Loyd Newcomb, 18432 Snohomish Ave., Snohomish, Wash. 98290.

DESCRIPTION OF THE PHOTOGRAPH

The new cultivar named 'Scented Springtime' is illustrated by the accompanying color photographs. The upper photograph shows a truss of flowers, taken indoors with a flash. The lower photograph shows a oblique side view of the entire plant, taken outdoors with flash in natural daylight. The whiteness of the petals is due to to overexposure, but the true color is seen in the opening buds.

Detailed Botanical Description of the Plant

The following botanical description of the new variety is based upon observations of plants grown in the ground in Langley, Wash. The plants were propagated in the greenhouse and then grown outdoors. The color references are from the R.H.S. Colour Chart.

Taxonomic status: Hybrid cultivar.

*Genus.*—Rhododendron.

*Seed parent.*—*R. keiskei* 'Yaku Fairy'.

*Pollen parent.*—R. 'Else Frye'.

Growth habit: Prostrate, vigorous growth forms a spreading mound to 30 cm. high and 1 m. broad.

Foliage: Leaf blade ovate, slightly revolute, base slightly retuse near midvein, 3–7 cm. long, 1–4 cm. wide. Upper surface with minutely impressed veins, glabrous, moderate olive green 146A. Lower surface dull, with abundant light scales and fewer dark brown scales, strong yellow green 143C. Petioles lepidote, 6–9 mm. long, 2 mm. thick.

Inflorescence: Terminal and subterminal clusters of 4–7 flowers per bud. Generally one, but up to three buds per terminus. Rachis 7 mm. long. Pedicels 1 cm. long. Bracts subtending individual flowers white, to 25 mm. long and 2 mm. wide.

Flower buds: Expanded bud 1.5 cm.×1.5 cm., ovoid. Bud scales lepidote, minutely white ciliate, moderate reddish orange 173B.

Calyx: Pentamerous. Lobes rounded, lepidote outside, ciliate, 7 mm. long×5 mm. wide, strong orange yellow 163B.

Corolla: Pentamerous, in a single whorl, glabrous inside, sparsely lepidote outside. Length measured along upper lobe 43 mm. overall, of which the tube length is 26 mm. and lobe length is 17 mm. Lobes 0.2 to 0.3 mm. thick. Flower spread 61 mm. when fully open, broadly funnel shaped. Color: Inside light greenish yellow 3D on upper lobe shading to 4D on lower lobes. Outside pale greenish yellow 1D.

*Markings.*—Two small spots of brilliant greenish yellow 1B at the bases of the valves of the upper lobes. Upper lateral lobes streaked with strong purplish red 63A to 63B, and blotched with strong to light purplish pink 63C to 63D. Other lobes occasionally streaked or blotched.

Reproductive organs:

*Androecium.*—Filaments white, 15–25 mm. long, pubescent at base. Anthers 3.5 mm. long×1 mm. wide, strong orange 168B.

*Gynoecium.*—Style 4–5 cm. long, pale greenish yellow 1D, glabrous. Stigma capitate, rugose, vivid yellow green 154A. Ovary 3 mm. long, densely lepidote, brilliant yellow green 149A.

Fruit: Thus far, this plant has proven to be sterile. Despite repeated efforts to breed this plant, no fruit has developed.

Blooming season: This cultivar is in peak bloom about mid-April in Seattle, Wash.

Hardiness: This cultivar has experienced temperatures as low as 11 degrees F. without damage to vegetative parts. This cold snap was unseasonably early and damaged many plants rated hardy to 5 degrees.

Color variation: This plant when grown in the greenhouse without exposure to cold temperatures produces nearly white flowers.

I claim:

1. A new and distinct variety of Rhododendron plant substantially as herein shown and described, characterized in particular by its prostrate growth habit and fragrant flowers.

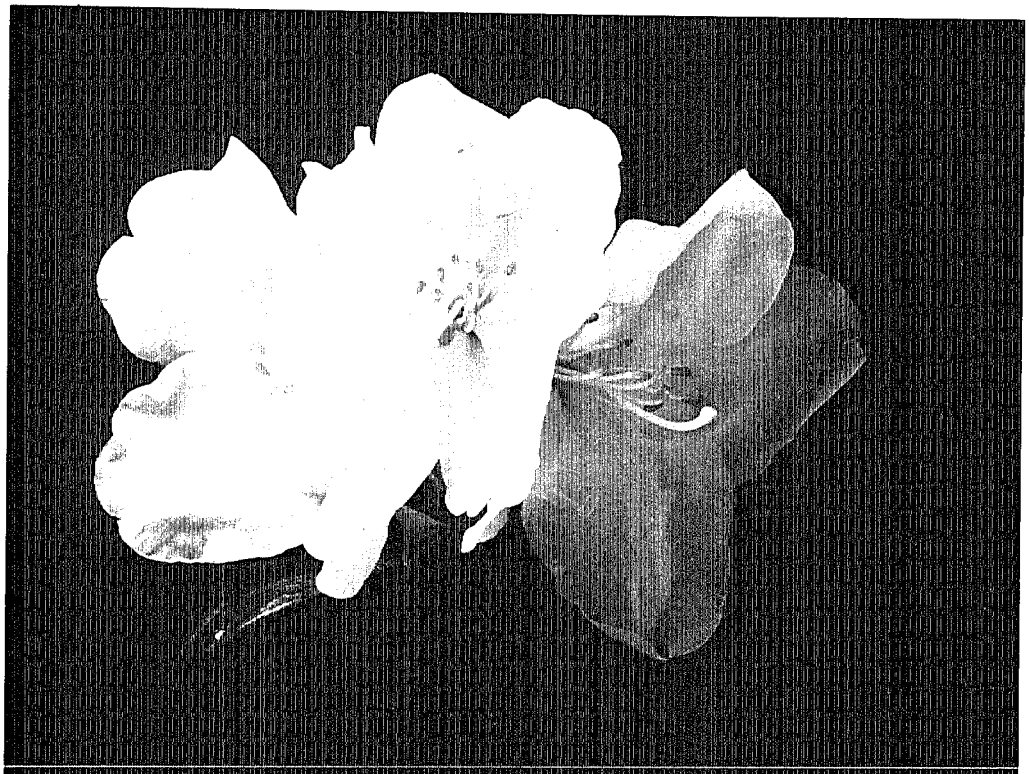
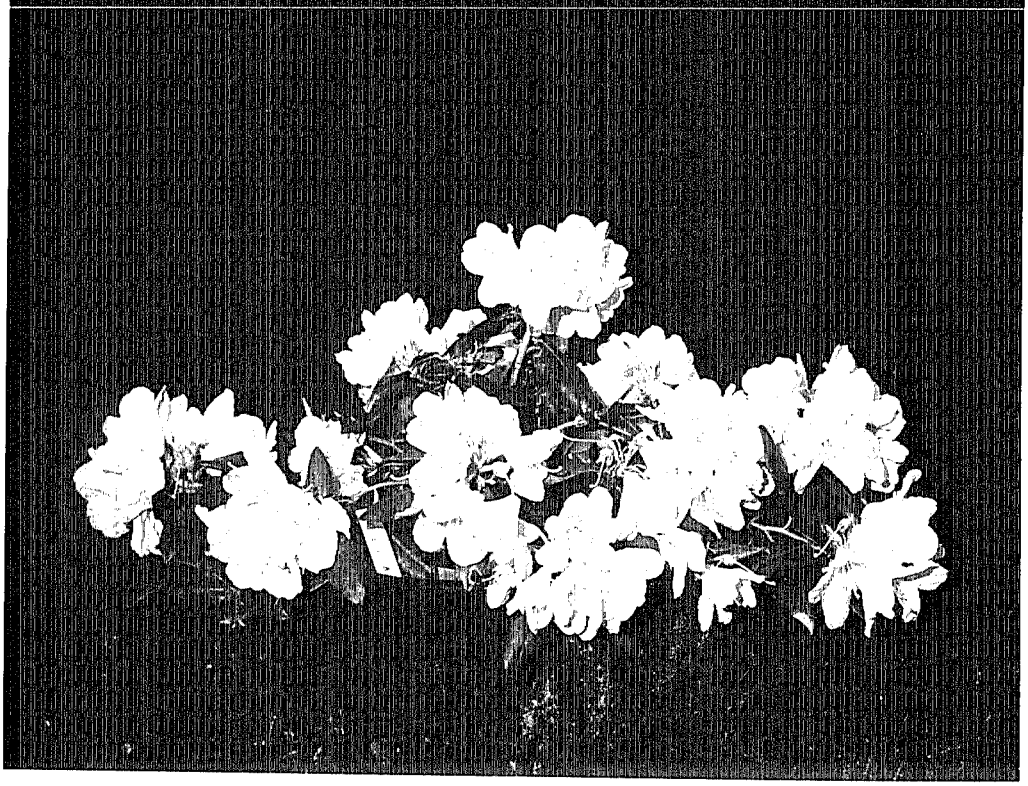

* * * * *